United States Patent
Lovat et al.

(10) Patent No.: US 10,408,848 B2
(45) Date of Patent: Sep. 10, 2019

(54) SKIN MODEL

(71) Applicants: Alcyomics Ltd, Newcastle upon Tyne Tyne And Wear (GB); University of Newcastle Upon Tyne, Newcastle upon Tyne (GB)

(72) Inventors: Penny Lovat, Newcastle upon Tyne (GB); David Hill, Newcastle upon Tyne (GB); Anne Dickinson, Newcastle upon Tyne (GB); Shaheda Ahmed, Newcastle upon Tyne (GB)

(73) Assignees: Alcyomics LTD (GB); University of Newcastle Upon Tyne (GB)

( * ) Notice: Subject to any disclaimer, the term of this patent is extended or adjusted under 35 U.S.C. 154(b) by 319 days.

(21) Appl. No.: 14/770,949

(22) PCT Filed: Feb. 27, 2014

(86) PCT No.: PCT/GB2014/050583
§ 371 (c)(1),
(2) Date: Aug. 27, 2015

(87) PCT Pub. No.: WO2014/132063
PCT Pub. Date: Sep. 4, 2014

(65) Prior Publication Data

US 2016/0003856 A1  Jan. 7, 2016
US 2016/0320419 A9  Nov. 3, 2016

(30) Foreign Application Priority Data

Feb. 27, 2013 (GB) .................................. 1303485.5

(51) Int. Cl.
| | | |
|---|---|---|
| *A01N 1/02* | (2006.01) | |
| *G01N 33/00* | (2006.01) | |
| *G01N 33/94* | (2006.01) | |
| *A61B 5/00* | (2006.01) | |
| *C12N 5/071* | (2010.01) | |
| *G01N 33/50* | (2006.01) | |
| *G09B 23/28* | (2006.01) | |

(52) U.S. Cl.
CPC .............. *G01N 33/94* (2013.01); *A61B 5/411* (2013.01); *A61B 5/445* (2013.01); *C12N 5/0698* (2013.01); *G01N 33/505* (2013.01); *G01N 33/5044* (2013.01); *G01N 33/5047* (2013.01); *G01N 33/5064* (2013.01); *G01N 33/5082* (2013.01); *G09B 23/28* (2013.01); *C12N 2502/094* (2013.01); *C12N 2502/1323* (2013.01); *C12N 2533/54* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 2004/0126405 A1 | 7/2004 | Sahatjian et al. | |
| 2005/0282148 A1* | 12/2005 | Warren ................ | C12N 5/0698 435/4 |
| 2008/0095748 A1 | 4/2008 | Kharazi et al. | |
| 2009/0016994 A1 | 1/2009 | Gibbs et al. | |
| 2009/0186089 A1 | 7/2009 | Lurvink et al. | |
| 2010/0297765 A1 | 11/2010 | Bechetoille et al. | |

FOREIGN PATENT DOCUMENTS

| | | | |
|---|---|---|---|
| DE | 10 2004 061289 A1 | 7/2006 | |
| EP | 1 375 647 A1 | 1/2004 | |
| EP | 2 243 825 A1 | 10/2010 | |
| EP | 2 573 167 A1 | 3/2013 | |
| GB | 2 485 816 A | 5/2012 | |
| GB | 1303485.5 | 8/2013 | |
| JP | 2006333763 A2 | 6/2005 | |
| WO | WO 2011/144956 A1 | 11/2011 | |
| WO | WO 2012069838 A1 * | 5/2012 | ........... G01N 33/505 |
| WO | WO 2013/014435 A1 | 1/2013 | |

OTHER PUBLICATIONS

International Search Report and Written Opinion dated Apr. 17, 2014 for Application No. PCT/GB2014/050583.
International Preliminary Report on Patentability dated Sep. 11, 2015 for Application No. PCT/GB2014/050583.
Aeby et al., Identifying and characterizing chemical skin sensitizers without animal testing: Colipa's research and method development program. Toxicol In Vitro. Sep. 2010;24(6):1465-73. doi: 10.1016/j.tiv.2010.07.005. Epub Jul. 17, 2010.
Fransson et al., Culture of human epidermal Langerhans cells in a skin equivalent. Br J Dermatol. Oct. 1998;139(4):598-604.

(Continued)

*Primary Examiner* — Amy E Juedes
(74) *Attorney, Agent, or Firm* — Wolf, Greenfield & Sacks, P.C.

(57) ABSTRACT

A three dimensional (3-D) model comprising a scaffold and autologous skin cells, the invention also provides methods of predicting immunogenicity and hypersensitivity or allergic or adverse immune reactions to potential therapeutic compounds, biologies, cosmetics and chemical sensitizers using the 3-D model of skin cells. The methods provide an in vitro assay employing autologous blood derived cells in the 3-D skin equivalent model and is of particular utility in the identification and prediction of skin sensitizers and in particular agents that may cause allergic contact dermatitis. The assay of the present invention provides inter alia methods of screening library compounds for sensitizing activity, identifying optimal therapeutics, especially but not exclusively, monoclonal antibodies and kits therefor.

6 Claims, 2 Drawing Sheets

(56) References Cited

OTHER PUBLICATIONS

Ouwehand et al., Technical advance: Langerhans cells derived from a human cell line in a full-thickness skin equivalent undergo allergen-induced maturation and migration. J Leukoc Biol. Nov. 2011;90(5):1027-33. doi: 10.1189/jlb.0610374. Epub Jun. 22, 2011.
Sun et al., Self-organization of skin cells in three-dimensional electrospun polystyrene scaffolds. Tissue Eng. Jul.-Aug. 2005;11(7-8):1023-33.

* cited by examiner

SKIN MODEL

RELATED APPLICATIONS

This application is a national stage filing under 35 U.S.C. § 371 of international application PCT/GB2014/050583, filed Feb. 27, 2014, which was published under PCT Article 21(2) in English.

The present invention relates to a three dimensional (3-D) model comprising skin cells, the invention also provides methods of predicting immunogenicity/adverse immune reactions and hypersensitivity or allergic reactions to potential therapeutic compounds, biologics, cosmetics and chemical sensitizers using the 3-D model of skin cells. The methods provide an in vitro assay employing blood derived cells in the 3-D skin equivalent model and is of particular utility in the identification and prediction of skin sensitizers and in particular agents that may cause allergic contact dermatitis. The assay of the present invention provides inter alia methods of screening library compounds for sensitizing activity, identifying optimal therapeutics, ie efficacy testing especially but not exclusively, biological therapeutic products, such as: antibodies, e.g. monoclonal antibodies, antibody conjugates, Fc fusions; or proteins, and kits therefor.

BACKGROUND

The delayed-type hypersensitivity reaction of Allergic Contact Dermatitis (ACD) can be acquired when a sensitized individual later becomes challenged with the same small molecule. ACD manifests itself during the phase of elicitation; following penetration of the epidermis and acquisition/processing by an antigen presenting cell (APC)—a specialized cell within the skin, which presents the allergen or antigen to other cells known as T cells recruited by chemokines to the skin, causing their activation and the production of high levels of lymphokines. These molecules give rise to a secondary response with skin inflammation and keratinocyte (skin cell) apoptosis. Distinct from its near relative, Irritant Contact Dermatitis (ICD), which is caused by irritants (e.g. soap, detergents, perfumes etc) and which can affect anyone who succumbs to sufficient exposure, ACD is influenced by environmental and genetic factors and may take many years to manifest, long after initial contact. With approximately 20% of the general adult population believed to be allergic to one or more chemical sensitizers, and with a growing list of novel cosmetic and pharmaceutical products becoming available, ACD threatens to be an increasing future occupational and consumer health problem. Developing suitable and sensitive methods for the assessment of a chemical's potential to cause ACD will be a crucial step in combating this disease. As regards to drug allergies, these are rarely detected in non-clinical studies and are usually only observed in Phase 3 clinical trials or during commercialization when larger populations are exposed to the drug. Although the number of drugs that elicit allergic reactions is relatively low, the potential impact is very high due to the late stage of development in which it is detected. Therefore, non-clinical methods to predict for the potential to produce allergic or adverse immune reactions are needed to help in compound selection.

There is currently no safe cost effective way to assess the allergenicity of novel compounds. The Patch Test creates patient discomfort and can trigger anaphylactic shock. Anaphylaxis, a severe and potentially life threatening reaction occurs in approximately 17,800 of the population each year as a result of exposure to substances to which the sufferer is allergic.

Identifying chemicals that have the potential to induce hypersensitivity skin reactions is a mandatory component of new product discovery by pharmaceutical and cosmetic industries. Historically, predictive testing has exclusively relied on in vivo animal testing. In the traditional guinea pig test, the product is painted on the body and the guinea pig is then injected with an additional chemical to help accentuate the effect of the test chemical in developing dermatitis. Alternatively in the mouse ear swelling test, the mouse's ears are painted with the test substance and its immunological response is determined by examination of lymph node tissue. However, with an EU ban on animal testing being implemented in March 2013, there is a pressing need for the development of alternative predictive in vitro and in silico techniques. Although it is known from the prior art to gage up and/or down regulation of gene products such as cytokines these assays are laborious and results are inconsistent. No validated in vitro model currently exists to predict immunogenicity and hypersensitivity or allergic reactions to potential therapeutic compounds, including monoclonal antibodies, cosmetics and chemical sensitizers.

3-D full thickness human skin models have been used for many years in toxicity testing. Current 3-D models use either: (i) keratinocytes and fibroblasts (derived from the epidermis or dermis respectively) from excess skin from plastic surgery patients or (ii) immortalised cell lines. In either instance, the cells are heterologous, and therefore cannot be truly predictive of a specified individual's response to a skin sensitizer or an allergic reaction. Indeed such assays tend to give a proportionately large number of false negatives.

There is therefore a need for an in vitro 3-D skin equivalent model and use of the model in an assay to discriminate between sensitizers and non-sensitizers and/or allergens and non-allergens for predicting the sensitizing nature of novel pharmaceutical, biologics, cosmetic and chemical products. There is a need for a simple, robust, cost-effective, accurate assay for testing novel compounds for hypersensitivity, allergic reactions and immunomodulatory capabilities.

There is especially a need for an autologous 3-D equivalent human skin model for use in personalised medicine and allergy/adverse immune reaction testing.

BRIEF SUMMARY OF THE DISCLOSURE

According to a first aspect of the invention there is provided a three dimensional (3-D) skin equivalent model, the model comprising a scaffold capable of supporting and maintaining a population of cells, wherein the cell population comprises autologous keratinocytes and fibroblasts derived from a skin biopsy sample.

Preferably, the skin biopsy sample is a scrape biopsy comprising a strip or square of skin or is a punch biopsy sample of approximately 4 mm in area and 2 mm in depth. It will be appreciated that the autologous dermally derived fibroblast and epidermally derived keratinocytes are prepared from the skin biopsy sample. More preferably, the biopsy sample is taken from a human subject. However, it will be appreciated that it is also possible that other mammalian species for which allergy testing in a veterinarian setting is required are equally applicable.

The present invention advantageously, by using scaffolds, surprisingly allows smaller numbers of cells to be 'seeded' for 3-D model development, it has been shown that sufficient cells can be generated from these very small biopsies for seeding on scaffold surfaces. The small size of the biopsies is particularly ideal in order to use the assay for a personalised medicine approach to therapy and testing of monoclonal antibody or immunomodulatory efficacy.

In one embodiment the scaffold comprises a tissue engineered collagen support although Alvatex® (Reinnervate Ltd) which is a highly porous polystyrene scaffold is also suitable. In an alternative embodiment the scaffold may comprise a native/natural acellular or decellularised collagen or collagen-like mesh or honeycomb. Any suitable scaffold may be used in the present invention providing that it possesses the appropriate characteristics of pore structure, pore size, ability to support cells and permit their invasion, infiltration, migration and proliferation.

In an alternative embodiment of the invention the 3-D skin equivalent model may also be seeded with additional cell populations also derived from the same biopsy sample.

According to a second aspect of the invention there is provided a method of preparing a 3-D skin equivalent model, the method comprising:
(i) isolating autologous keratinocytes and fibroblasts from a skin biopsy sample;
(ii) storing the isolated keratinocytes;
(iii) seeding a scaffold with the isolated fibroblasts under culture conditions and allowing a sufficient period of time to permit production of an extracellular matrix;
(iv) seeding the scaffold comprising the fibroblasts with the keratinocytes; and
(v) culturing the seeded scaffold under appropriate conditions.

It will be appreciated that keratinocytes and fibroblasts are isolated from the same skin sample.

Preferably, culturing steps are under flow conditions.

The method of preparing the 3-D skin equivalent model of the invention advantageously results in a product that has increased longevity up to 5 months or so over a skin biopsy sample.

According to a third aspect of the invention there is provided an in vitro method for identifying chemical compounds that are sensitizers or for discriminating between chemical compounds that are sensitizers and non-sensitizers, the method comprising:
(i) preparing a donor blood sample so as to isolate a population of T cells and monocyte-derived dendritic cells therefrom;
(ii) incubating the monocyte-derived dendritic cells with a test compound;
(iii) incubating the compound treated monocyte-derived dendritic cells with a population of T cells isolated in step (i);
(iv) incubating the mixed T cell and compound treated monocyte-derived dendritic cells with a 3-D skin equivalent model that comprises keratinocytes and fibroblasts isolated from an autologous biopsy sample obtained from the same donor; and
(v) assessing hypersensitivity and allergic reactions by graded histological changes in the 3-D skin equivalent model as compared to a control.

Preferably, the T cells and monocyte-derived dendritic cells (DCs) are isolated from peripheral blood mononuclear cells (PBMC). For example and without limitation, the T cell and monocyte-derived dendritic cells may be separated from PBMC by magnetic activated cell sorting or similar techniques. Preferably, the dendritic cells are either standard or fast matured dendritic cells.

Preferably, the first incubating step of step (ii) is for between 2 to 24 hours. Typical incubation conditions are carried out at 37° C. in a humidified 5% $CO_2$ air incubator, a typical culture medium is Roswell Park Memorial Institute 1640 (RPMI 1640, Gibco UK) containing 100 IU/ml penicillin, 100 µg/ml streptomycin (Gibco UK) and 2 mM L-glutamine (Gibco UK) supplemented with 10% v/v heat inactivated foetal calf serum (FCS, Sera Lab). or Ex Vivo (Gibco UK) serum free medium. The culture conditions are non-limiting in so far as other variations in conditions that allow for growth and maintenance of the cells are equally applicable.

Preferably step (ii) further includes, as a control incubating a further or second set of monocyte-derived dendritic cells with a compound that is a known non-sensitizer. Alternatively the control may be monocyte-derived dendritic cells incubated with no additional chemical compounds at all.

Preferably, the second incubating of step (iii), comprising incubating DCs with a population of T cells isolated in step (i) is for between 3-7 days using the same culture conditions as for step (ii) except that 10% heat inactivated autologous serum, human AB serum, or an equivalent thereof is used and replaces foetal calf serum. In the instance where a control comprises DCs with a population of T cells isolated in step (i) having been exposed to a non-sensitizer, this further or second set of cells is incubated in identical conditions to the test mixture.

Preferably, the third incubating step of step (iv), comprising incubating the mixed T cell and DCs cells with an autologous 3-D skin equivalent model biopsy sample, prepared according to the second aspect of the invention, is for between 1 to 3 days. In the instance where a control comprises DCs having been exposed to a non-sensitizer, the cells are incubated with the 3-D skin equivalent model in identical conditions to the test mixture.

Preferably, the step of assessing hypersensitivity and allergic reactions in the 3-D skin equivalent model by graded histological changes comprises assessment of vacuolisation of epidermal cells, damage to basal keratinocytes and connection between the epidermis and dermis. In one embodiment of the invention, the histological Grades are I to IV, wherein grade I is negative and Grades II to IV are varying degrees of positive. Preferably, Grade I is defined as the skin biopsy showing very mild vacuolisation of epidermal cells, Grade II is defined as the skin biopsy showing diffuse vacuolisation of epidermal cells, Grade III is defined as the skin showing cleft formation between the epidermis and dermis caused by confluent vacuolar damage to basal keratinocytes and Grade IV is defined as the skin showing the complete separation of the epidermis and dermis. FIGS. 1*a*-1*d* illustrate the histologically graded damage. Alternatively another grading system may be used.

Preferably, the control value may be derived from the group comprising:
(i) a further or second set of monocyte-derived dendritic cells that have been incubated in step (ii) with a compound that is a known non-sensitizer;
(ii) a further or second set of monocyte-derived dendritic cells that have been incubated in step (ii) with no additional chemical compounds;
(iii) a 3-D skin equivalent model that has been incubated with autologous lymphocytes; or
(iv) a skin 3-D skin equivalent model that has been incubated with compound alone at the same concentrations as that used in step (ii).

Preferably, the test compound value is compared to the control value so that an increase or decrease from the control value is indicative of a sensitizing reaction.

According to a fourth aspect of the invention there is provided an in vitro method of identifying chemical compounds that are sensitizers or non-sensitizers and/or allergens or non-allergens, the method comprising:
  (i) separating a population of monocyte-derived dendritic cells from a donor blood sample comprising a population of T cells;
  (ii) incubating the monocyte-derived dendritic cells with a test compound;
  (iii) incubating the compound treated monocyte-derived dendritic cells of (ii) with the separated donor blood sample of (i);
  (iv) determining the level of T cell proliferation and/or IFN-γ expression in the sample of (iii), wherein the level of T cell proliferation and/or IFN-γ expression correlates with a defined grade of histological change observed in a 3-D skin equivalent model, prepared according to the second aspect of the invention, treated with said test compound; and
  (v) comparing the level of T cell proliferation in the sample with the level of T cell proliferation in at least one control sample treated with a control sensitizer compound and at least one control sample treated with a control non-sensitizer compound and/or at least one control sample treated with a control allergen compound and at least one control sample treated with a control non-allergen compound; or
  (vi) comparing the level of IFN-γ expression in the sample with the level of IFN-γ expression in at least one control sample treated with a control sensitizer compound and at least one control sample treated with a control non-sensitizer compound and/or at least one control sample treated with a control allergen compound and at least one control sample treated with a control non-allergen compound,
  wherein comparison of T cell proliferation and/or IFN-γ expression in the sample with T cell proliferation and/or IFN-γ expression in the control samples identifies the test compound as a sensitizer or non-sensitizer and/or an allergen or non-allergen.

By comparing the level of T cell proliferation and/or the level of IFN-γ expression induced by a test compound to levels induced by a sensitizing and non-sensitizing control compound (or allergen or non-allergen control compound), the method allows prediction of the sensitizing capability of the test compound. The use of sensitizing and non-sensitizing control compounds (or allergen or non-allergen control compound), advantageously provides thresholds values for sensitizing and non-sensitizing and/or allergic and non-allergic levels of T cell proliferation and IFN-γ expression.

Preferably, the level of T cell proliferation determined in (iv) correlates with a defined grade of histological change observed in a 3-D skin equivalent model treated with said compound. More preferably, the level of T cell proliferation in the 3-D skin equivalent model treated with said compound correlates with an LLNA class observed in a LLNA mouse model treated with said compound.

Preferably, the level of IFN-γ expression determined in (iv) correlates with a defined grade of histological change observed in a skin explant treated with said compound. More preferably, level of IFN-γ expression in the 3-D skin equivalent model treated with said compound correlates with a LLNA class observed in a LLNA mouse model treated with said compound.

Preferably, each of said control compounds is administered in a concentration such that at least 70% of treated cells remain viable 24 hours after exposure to the compound. More preferably, at least 75% of treated cells or at least 80% of treated cells remain viable 24 hours after exposure to the compound. Still more preferably, 85, 90 or 95% of treated cells remain viable 24 hours after exposure to the compound.

Preferably, the percentage of viable cells is determined using a cell viability assay.

Preferably the cells of the cell viability assay are peripheral blood mononuclear cells, more preferably blood mononuclear-derived monocytes, and more preferably monocyte-derived dendritic cells.

Preferably, the level of T cell proliferation is determined by [$^3$H] thymidine incorporation. Alternative methods of measuring T cell proliferation include flow cytometric assessment and by an enzyme-linked immunoabsorbent assay (ELISA) based on bromo-2'-deoxyuridine (BrdU) incorporation.

Preferably, IFN-γ expression is determined by flow cytometry. Alternative methods of measuring IFN-γ production can be by ELISA, ELISPOT and real-time RT-PCR.

Preferably, the dendritic cells are either standard or fast matured dendritic cells.

Preferably, the first incubating step of step (ii) is for between 2 to 24 hours. Typical incubation conditions are carried out at 37° C. in a humidified 5% $CO_2$ air incubator, a typical culture medium is Roswell Park Memorial Institute 1640 (RPMI 1640, Gibco UK) containing 100 IU/ml penicillin, 100 µg/ml streptomycin (Gibco UK) and 2 mM L-glutamine (Gibco UK) supplemented with 10% v/v heat inactivated foetal calf serum (FCS, Sera Lab). or Ex Vivo (Gibco UK) serum free medium. The culture conditions are non-limiting in so far as other variations in conditions that allow for growth and maintenance of the cells are equally applicable.

Preferably, the incubation of step (ii) comprises incubation with 10% heat inactivated fetal calf serum.

Preferably, the second incubating of step (iii) is for between 3-7 days. Preferably, the second incubating of step (iii), comprising incubating DCs with a population of T cells isolated in step (i) is for between 3-7 days using the same culture conditions as for step (ii) except that 10% heat inactivated autologous serum, human AB serum, or an equivalent thereof is used and replaces foetal calf serum. In the instance where a control comprises DCs with a population of T cells isolated in step (i) having been exposed to a non-sensitizer, this further or second set of cells is incubated in identical conditions to the test mixture.

Preferably, the incubation of step (iii) comprises incubation with 10% heat inactivated autologous serum, human AB serum, or an equivalent thereof serum.

Preferably, the control sample comprises a further or second set of monocyte-derived dendritic cells that have been incubated in step (ii) with the control compound(s). More preferably, said further or second set of monocyte-derived dendritic cells are separated from the donor blood sample of step (i). Alternatively the control may be monocyte-derived dendritic cells incubated with no additional chemical compounds at all.

According to a fifth aspect of the invention there is provided an in vitro method for detecting allergic reactions to a monoclonal antibody or monoclonal antibody biosimilars therapy, the method comprising using the 3-D skin equivalent model of the first aspect of the invention incubated with autologous peripheral blood derived mononuclear cells or reactive cells from a mixed lymphocyte reaction in the presence of the monoclonal antibody or monoclonal antibody biosimilars and comparing a reaction to a control value.

According to a sixth aspect of the invention there is provided an in vitro method of assessing efficacy of a biological therapeutic product, the method comprising using the 3-D skin equivalent model of the first aspect of the invention incubated with autologous peripheral blood derived mononuclear cells or reactive cells from a mixed lymphocyte reaction in the presence of the biological therapeutic product and comparing a reaction to a control value, and repeating the method over a period of time.

A number of chimeric, human and humanised monoclonal antibody products have received FDA approval for use in disease states including cancer, cardiovascular disease, systemic lupus erythematous, transplant rejection, macular degeneration, psoriasis, auto-immune disorders and rheumatoid arthritis. A number of new biological therapeutic products are in development, and all require extensive testing prior to clinical trial and release onto the market, there is currently no known assays for assessment of monoclonal antibody allergenicity. However, the 3-D skin equivalent model of the present invention and the methods of the present invention provide the first real predictive assay for such therapeutic products and offer immediate advantage to the pharmaceutical industry, patients and clinicians alike.

Preferably, the method of assessing biological therapeutic product is for selecting an appropriate biological therapeutic product, e.g monoclonal antibody therapy for an individual suffering from a disease selected from the group comprising cancer, cardiovascular disease, systemic lupus erythematosus, transplant rejection, macular degeneration, psoriasis, auto-immune disorders and rheumatoid arthritis.

According to a seventh aspect of the invention there is provided a method of treating an individual suffering from a disease selected from the group comprising cancer, cardiovascular disease, systemic lupus erythematosus, transplant rejection, macular degeneration, psoriasis, auto-immune disorders and rheumatoid arthritis, the method comprising using the 3-D skin equivalent model of the first aspect of the invention in a method according to the fifth or sixth aspect of the invention to select biological therapeutic product to which the patient will respond without a side effect of allergenicity.

According to a eighth aspect of the invention there is provided a kit comprising a scaffold onto which keratinocytes and fibroblasts may be seeded, a means for separating monocytes from a blood sample and instructions for use thereof. More preferably, said means for separating monocytes comprises a CD14$^+$ cell separation kit and at least one control sensitizer compound and at least one control non-sensitizer compound and/or at least one control allergen compound and at least one control non-allergen compound.

Preferably, the kit further comprises a means for standard or fast dendritic cell maturation and instructions for use thererof.

Preferably, that at least one control sensitizer compound and at least one control non-sensitizer compound and/or at least one control allergen compound and at least one control non-allergen compound of the kit are located in defined positions on a solid support. More preferably, said solid support is a 6, 12, 24, 48 or 96 well plate.

Preferably, the kit comprises at least two control sensitizer compounds, wherein said compounds are DNCB and NiSO4.

Preferably, the kit comprises at least two control non-sensitizer compounds, wherein said compounds are Triton-X and ZnSO4.

Still more preferably, the kit comprises at least two control sensitizer compounds, wherein said compounds are DNCB and NiSO4 and at least two control non-sensitizer compounds, wherein said compounds are Triton-X and ZnSO4.

Features ascribed to any aspect of the invention are applicable mutatis mutandis to all other aspects of the invention.

BRIEF DESCRIPTION OF THE DRAWINGS

Embodiments of the invention are further described hereinafter with reference to the accompanying drawings, in which:

FIG. 1 shows histopathological changes for different grades of skin graft versus host reaction (GVHR)

DETAILED DESCRIPTION

Figure 1A:
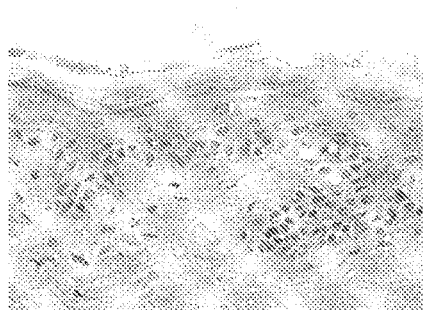
FIG. 1A shows Grade I skin GVHR showing very mild vacuolisation of epidermal cells (Negative reaction)
Figure 1B:
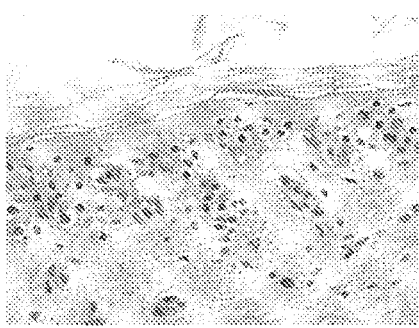
FIG. 1B shows Grade II skin GVHR showing diffuse vacuolisation of epidermal cells (Positive reaction)
Figure 1C:
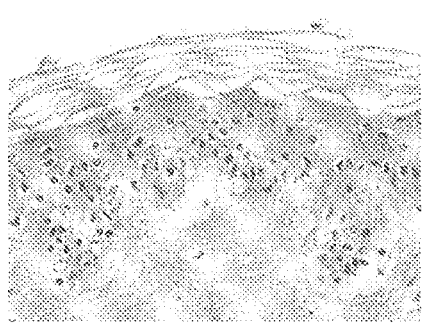
FIG. 1C shows Grade III skin GVHR showing cleft formation between the epidermis and dermis caused by confluent vacuolar damage to basal keratinocytes (Positive reaction)
Figure 1D:
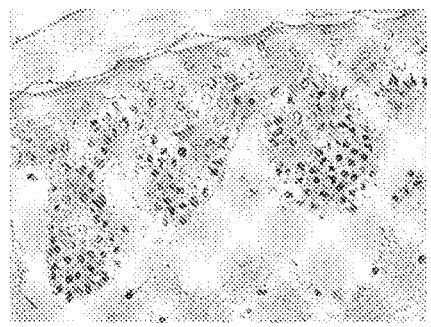
FIG. 1D shows Grade IV skin GVHR showing the complete separation of the epidermis and dermis (Positive reaction).

Reference herein to "scaffold" means any 3-D structure either native/natural or tissue engineered that is capable of supporting cell migration, cell infiltration and/or cell proliferation.

Reference herein to "autologous" means that the blood derived products and skin explants are derived or collected from the same individual.

Reference herein to a "sensitizer" includes any chemical compound or chemical agent or antibody that causes a substantial proportion of exposed people or animals to develop an allergic reaction in normal tissue after single or repeated exposure to the said compound, antibody or chemical agent.

Reference herein to an "allergen" and "allergenic" includes any foreign substance such as an environmental substance or chemical that is capable of inducing allergy or a specific hypersensitive reaction in the body. Common allergens include plant pollens, spores of mold, animal dander, house dust, foods, feathers, dyes, soaps, detergents, cosmetics, plastics, and drugs. Allergens can enter the body by, for example, being inhaled, swallowed, touched, or injected.

Reference herein to a "chemical compound" is intended to include a chemical, therapeutic, pharmaceutical, biologic, antibody or cosmetic agent, substance, preparation or composition.

Reference herein to a "biologic" is intended to include a preparation, such as a drug, a vaccine, serum or an antitoxin, that is synthesized from living organisms or their products and used as a diagnostic, preventive, or therapeutic agent.

Reference herein to "biological therapeutic products" includes, but is not limited to, antibodies, e.g. monoclonal antibodies, antibody conjugates, Fc fusions; or proteins or protein based therapeutics.

We have previously shown that following incubation of chemicals with blood derived dendritic cells or mononuclear cells with monoclonal antibodies then interaction with T cells (in the first instance for chemical sensitisation) and then with skin in the second phase of the reaction it is possible to observe a histopathological damage read out. The prejudice in the art was that it was only possible to show skin sensitisation or allergy to chemicals or other allergies using skin dendritic cells. The prejudice arises from the fact that far fewer dendritic cells can be obtained from skin biopsies than can be prepared from monocytes in whole blood. In the present invention, with improved technology to enable 3-D skin equivalent models to be developed, we provide for the first time an autologous 3-D skin equivalent model that surprising comprises less cells, with increased longevity that can be used as a robust and accurate system for detecting allergic and sensitizing reactions.

The present invention conveniently provides a 3-D skin equivalent model of autologous mammalian skin cells that can be used in an in vitro assay and methods which allows for the study of primary and secondary immune responses in the presence of potential sensitizing compounds thereby advantageously reducing the need for extensive animal testing.

The present invention conveniently provides a 3-D skin equivalent model of autologous mammalian skin cells from a specified individual that can be used in an in vitro assay to assess that individual's response to a particular chemical compound or therapeutic agent and also to monitor the efficacy of any treatment regime.

The present invention is of particular utility to an individual who is about to receive antibody or biologic therapy, in particular but not exclusively an individual suffering from chronic rheumatoid arthritis who is to receive antibody therapy. The present invention will allow a clinician to assess which antibody therapy will be tolerated and which antibody therapy may cause an allergic reaction. It is envisaged that the problem associated with unpredictable allergic reactions to antibody therapy will be overcome by the use of the 3-D skin equivalent model of autologous skin cells of the present invention.

The ability to grown whole skin models from constituent cells rather than individual punch biopsy sample has many advantages. For example, using a single sample of skin tissue to create an autologous 3-D skin equivalent model with extended longevity it will be possible to use the 3-D model in multiple tests over a period of months rather than a single sample for use in only one assay. The 3-D skin equivalent model is viable over many months rather than weeks in the standard skin biopsy model. It is envisaged that a further advantage is that culturing under flow conditions will achieve a faster cell culture with increased proliferation rates and improved cell viability which will not only reduce the time taken and cost of testing but will also permit repeated dose testing for allergenicity. Using the longer viable 3-D skin equivalent model of the present invention will enable the efficacy of therapy to be assessed over time without the requirement for a further skin biopsy sample being taken from an individual, the only further requirement being a peripheral blood sample. This is of benefit to the individual undergoing the test as it will minimize any pain due to taking of a biopsy sample.

The products and methods of the present invention are unique and gives insight into the use of a blood based assay on a 3-D autologous skin equivalent model for predicting response to chemical sensitizers and to investigate their potential allergic/inflammatory signals. The present invention provides a blood based assay and 3-D skin equivalent model that improves on the current techniques and provides a novel means of testing novel drugs for hypersensitivity and allergic reactions.

The product and assay of the present invention provides the advantage over a heterologous three dimensional skin equivalent model as it uses blood with autologous immune cells and autologous skin cells enabling immune responses to be studied and cellular and molecular targets identified thus aiding in drug discovery, improving drug design and optimisation for drug dosage prior to a clinical trial.

Viability Assay

A dye exclusion method can be used to investigate cell viability. It is based on the principle that live cells possess intact cell membranes that exclude certain dyes, such as trypan blue, eosin, or propidium, whereas dead cells do not. Cells are treated with different concentrations of the test substance for a period of 24 hours. Cells are harvested and an aliquot of the cell suspension is mixed with trypan blue (1:1) and then visually examined to determine whether cells take up or exclude dye. The trypan blue chromopore is negatively charged and cannot react with a cell unless the cell membrane is damaged, therefore a viable cell has a clear cytoplasm whereas a non-viable cell has a blue cytoplasm. A total of 100 cells are counted. The unstained (viable) and stained (non-viable) cells are counted separately using a haemocytometer and viability recorded. By culturing cells in the presence of the test reagents any adverse effect of the reagents on cell viability can be observed. Cell viability of 70% or more is regarded as adequate for the methods of the present invention. Preferably, the cell viability is 75% or more or 80% or more.

Preparation of Peripheral Blood Mononuclear Cells (PBMC)

Peripheral Blood Mononuclear cells (PBMC) from blood obtained from healthy volunteers was prepared by density-gradient centrifugation using Lymphoprep™ solution (Axis-Shields) and diluted 1:1 in Earle's balanced salt solution (EBBS) (Sigma). Mononuclear cells were collected from the density medium:plasma interface and washed in cold PBS and counted using an Improved Neubauer cell counting chamber (Weber Scientific International Ltd., UK). Cell viability was assessed by trypan blue (Gibco).

Separation of CD14+ Monocytes Using the MACS® Technology

The MACS® (Magnetic-activated cell sorting) technology (Miltenyi Biotec) uses columns filled with magnetic particles to separate magnetically labelled cells. For the separation process these columns are placed in a strong magnetic field (QuadroMACS® separator). Required amount of PBMC were transferred to a fresh 50 ml falcon tube, topped up with PBS and strained through a 100 μm nylon filter to remove any clumps. A maximum of $100 \times 10^6$ mononuclear cells were washed and re-suspended in cold MACS buffer (PBS containing 0.5% FCS and 1 mM ethylene diamine tetracetic acid (EDTA) resusupended in 80 μl buffer/$10 \times 10^6$ cells. The cells were incubated at 2-8° C. for 20 minutes with 10 μl/$10 \times 10^6$ cells CD14 antibody coupled with magnetic microbeads. The cell suspension was added to the column allowing the negative cells to pass through for collection (as the "T cell" fraction and the positive cells (CD14+) were then collected and assessed for purity by flow cytometry analysis.

Generation of Monocyte-Derived Dendritic Cells (moDC)

CD14 positive monocytes purified by MACS® separation were cultured in a 24 well plate at a density of $0.5 \times 10^6$/ml in culture medium with 50 ng/ml GM-CSF and 50 ng/ml IL-4. After 3 days 400 µl of the medium were carefully removed and 500 µl fresh medium containing 50 ng/ml GM-CSF and 50 ng/ml IL-4 (Immunotools) were added and left for a further 3 days. After 6 days immature antigen presenting cells dendritic cells (DC) were either collected or allowed to mature by adding lipopolysaccharides (LPS) (0.1 µg/ml, Sigma), IL-1β (10 ng/ml, Immunotools) and TNFα (10 ng/ml, Immunotools) for a further 24 hours.

Generation of Mature Fast DC

CD14 positive selection cells were put into culture (0.3-0.5×10$^6$ cells per well in 24 well plate) with RP-10 medium supplemented with IL-4 (50 ng/ml) and GM-CSF (50 ng/ml). After 24 hours maturation cytokines TNF-α (10 ng/ml), IL-1β (10 ng/ml), IL-6 (10 ng/ml), 1 uM PGE2, Resiquimod (2.5 µg/ml), CD40L (1 µg/ml) and LPS (0.1 µg/ml) were added to each well for a further 24 hours.

T Cell Proliferation Assays

Mature Fast DC treated and untreated with compounds as well as cells from both allogeneic and autologous sources in triplicate at a ratio of 1:10 (DC:T cells) in (200 µl total volume) in 96-well round-bottomed plates for 5 days at 37° C. in a humidified 5% $CO_2$ in air incubator. After 5 days, 40 µl of supernatant was removed from the top of each triplicate well and stored at −20° C. for further cytokine analysis. [$^3$H]-Thymidine (used at a concentration of 3.7 MBq/ml) was then added to each well using appropriate radiation protection methods and allowed to incubate for 16-18 hours at 37° C. in a humidified 5% $CO_2$ in air incubator. Cells were harvested and subsequently counted using the 1450 Micro-Beta TriLux Microplate Scintillation and Luminescence Counter (PerkinElmer®). Data was interpreted using Graphpad Prism® software.

Skin Biopsy

Sections from a 4 mm wide 2 mm deep skin punch biopsy were obtained from an individual. Ideally the skin punch biopsy is obtained from an area of medium skin thickness and low innervations so as to cause as little discomfort as possible to the individual. Autologous keratinocytes and fibroblasts are separated from the biopsy sample Generation of Keratinocytes and Fibroblasts Autologous keratinocytes and fibroblasts were generated from a 4 mm punch skin biopsy, the skin biopsies were incubated with dispase (final concentration 1 mg/ml) at 4° C. overnight. Following the incubation dispase was removed by washes then the epidermis was peeled from the dermis using sterile forceps. The epidermis was used for generating keratinocytes and dermis used for generating fibroblasts. The epidermis was incubated at 37° C. with Trypsin/EDTA and dermis incubated with collagenase (100 U/ml) to release the keratinocytes and fibroblasts from the tissue matrix into the supernatant. The cells were collected from supernatants following centrifugation. Collected keratinocytes and fibroblasts were cultured with appropriate medium in a 48 or 24 well culture plate as passage 0. The medium used for growing keratinocytes is EpliLIfe™ (Life technologies) and for fibroblasts is Dulbecco's Modified Eagles Medium (DMEM) (Sigma) "containing 100 IU/ml penicillin, 100 µg/ml streptomycin (Gibco UK) and 2 mM L-glutamine (Gibco UK) supplemented with 10% v/v heat inactivated foetal calf serum (FCS, Sera Lab) respectively. Both keratinocytes and fibroblasts would adhere to the plastic surface and have a monolayer growth. The cells were fed twice a week till they reached approx 80% confluence. Then the cells were removed from the culture wells using Trypsin/EDTA. The cells were then collected, washed and reseeded into a larger tissue culture well or a flask as passage 1 to expand further on for example 12 or 24 well scaffold inserts. The cells have been expanded up to passage 3 to obtain 0.5-2×10$^6$ cells. The successful rate of generating keratinocytes from punch skin biopsies is 60%.

The skin explant assay consisted of co-incubating the treated and untreated DC cells with T cells from the same donor for 7 days. After this time the T cells are added in 96 well plates or 12 or 24 well inserts to sections of the 3D human skin equivalent model. The skin equivalent model is co-incubated for three days and then routinely stained for histopathology. 3-D skin equivalent models incubated with medium alone or autologous cells alone are used as controls. The 3-D skin equivalent model is then routinely sectioned and stained for graded histopathological damage using a criteria which is very similar to that used and observed in the clinical setting with distinct pathological damage.

In the present invention DC response to chemical sensitizers versus known non-sensitizers can be assessed by their effect on sensitized cells by assessment in vitro of graded skin damage.

3-D Skin Equivalent Model Culture

Human dermal fibroblasts isolated from dermis of the skin are seeded onto a scaffold and cultured for 3 weeks to allow production of the extracellular matrix (ECM). Keratinocytes from the same piece of skin are isolated (0.5-5×10$^6$) and cryopreserved and at 3 weeks thawed and seeded onto the scaffold, raised to the air-liquid interface, and assessed for growth over 2-5 months. To aid differentiation and growth and use of cell flow conditions at a rate of 100-500 ul/min to increase longevity is also employed.

Processing Skin

Preparation of 3T3 Cells

3T3 cells (3T3-J2 strain (ATCC# CCL-92)) were grown as feeder cells for keratinocytes. 3T3 cells were grown in 3T3 medium (DMEM supplemented with 10% new-born calf serum, 1% Penicillin-Streptomycin-Fungizone). 3T3 cells were maintained in sub-confluent culture to prevent spontaneous transformation. Medium was replaced every 3-4 days. A flask of 70% confluent 3T3 cells treated with Mitomycin-C (0.4 µg/ml) for 2 hours at 37° C. was prepared before processing epidermis.

Processing Skin

Skin was washed and cleaned with PBS and fat removed leaving a thin layer of epidermis and dermis. Skin was then incubated overnight with Dispase (1 mg/ml) at 4° C. The next day skin was removed from the well and epidermis peeled backusing forceps.

Processing Epidermis

A flask of 70% confluent 3T3 cells was prepared in advance of processing the epidermis. The peeled epidermis was incubated for 5 minutes at 37° C. with Trypsin/EDTA (T/E). After 5 minutes a serological pipette was used to disrupt the tissue and release cells into the supernatant. Trypsin/EDTA was neutralised by adding 200 ul FCS and 10 mls PBS. Epidermis was removed with a tip and discarded. Supernatant was centrifuged at 500 g for 5 minutes. Supernatant was discarded and the cell pellet resuspended in 20 ml pre-warmed F-Media. 3T3 medium was removed from 3T3 cells treated with mitomycin-C, rinsed X2 with PBS and the resuspended pellet in F-Media was added to the flask. Cells were grown until keratinocytes became visible. Keratinocytes were then removed from the 3T3 cells by trypsination and further cultured in EpiLife medium until the required numbers of cells (2×10$^6$) were acquired. Cells should be between passages 0-3.

Processing Dermis

The remaining dermis (after the epidermis peel) was cut into square pieces using a scalpel and placed in to 3 mls RF10 and collagenase enzyme (100 U/ml) and incubated overnight at 4° C. The next day tissue was disrupted using a serological pipette. The supernatant was passed through a cell strainer (100 micron) and centrifuged at 500 g for 5 minutes. The cell pellet was re-suspended in 1 ml DMEM (DMEM+Glut+P/S+20% FCS). Cells were cultured until the required numbers of fibroblasts ($0.5 \times 10^6$) were acquired. Cells should be between passages 0-7.

3D Skin Equivalent Model

Alvetex Scaffold Preparation

Alvetex was soaked in 70% ethanol for 5 minutes and washed twice in 8 mls DMEM for 2 minutes each. Alvetex was then placed into a 6 well plate.

Adding Fibroblasts to Alvetex Scaffold

Fibroblasts were grown to maximum of passage 7 in DMEM to 70% confluence. Fibroblasts were trypsinised with T/E (2 minutes at 37° C.). Cells were centrifuged as before and $0.5 \times 10^{*}6$ cells were removed and placed in 100 ul volume DMEM. Fibroblasts were added to the centre of the scaffold. The plate was incubated for 3 hours to allow the cells to attach to the scaffold. The well was then flooded with 8 mls DMEM. Medium was replaced every 2 days for at least 21 days. After 21 days, fibroblast monolayer (dermis) was formed and ready for the addition of keratinocytes.

Adding Keratinocytes to Alvetex Scaffold

Figure 2:
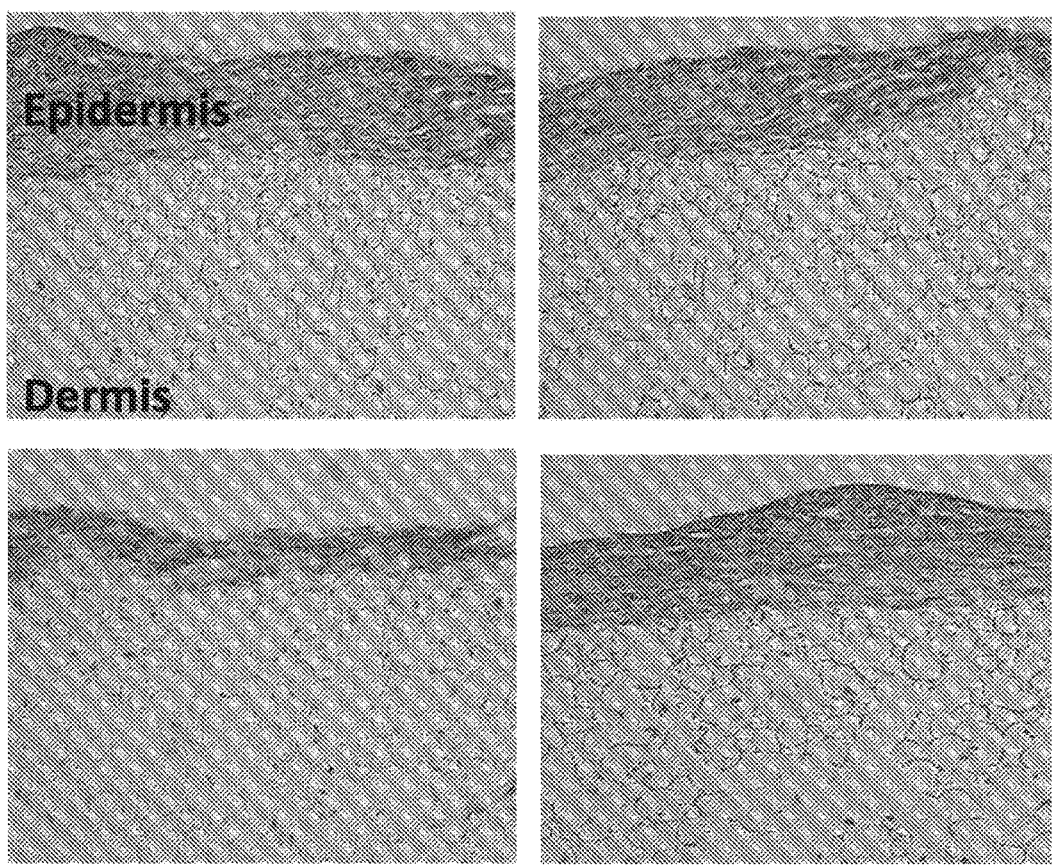
FIG. 2 shows 3D skin equivalent sections that have been formalin fixed. Sections were paraffin embedded, sectioned and stained with haematoxylin and eosin.

Keratinocytes were grown to maximum of passage 3 in Epilife to 70% confluence. Keratinocytes were then trypsinised with T/E (2 mins at 37° C.). Cells were centrifuged as before and $2 \times 10^{*}6$ cells were removed and placed in 100 ul volume F-Media. Media was removed from the well containing the Alvetex scaffold and keratinocytes were added to the centre of the scaffold. The well was flooded with 4 mls F-Media. The plate was incubated for 3 hours to allow the cells to attach to the scaffold. The well was then flooded with another 5 mls F-Media. The plate was incubated for 3 days. After 3 days medium was removed and replaced with 4 mls F-Media to allow cells exposure to air-surface interface. Medium was replaced every 2 days for at least 14-18 days. After 18 days, 3D skin equivalent was cut out of the plastic holder and formalin fixed. Sections were paraffin embedded, sectioned and stained with haematoxylin and eosin as shown in FIG. 2.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An in vitro method for identifying chemical compounds that are sensitizers or for discriminating between chemical compounds that are sensitizers and non-sensitizers, the method comprising:
   (i) preparing a donor blood sample so as to isolate a population of T cells and monocyte-derived dendritic cells therefrom;
   (ii) incubating the monocyte-derived dendritic cells with a test compound;
   (iii) incubating the compound treated monocyte-derived dendritic cells with a population of T cells isolated in step (i);
   (iv) establishing a 3-D skin equivalent model that comprises a monoculture of fibroblasts grown in monoculture on matrix for at least 21 days and subsequently seeded with keratinocytes, wherein both fibroblasts and keratinocytes are isolated from an autologous biopsy sample obtained from the same donor;
   (v) incubating the mixed T cell and compound treated monocyte-derived dendritic cells with the 3-D skin equivalent model of step (iv) that comprises keratinocytes and fibroblasts isolated from an autologous biopsy sample obtained from the same donor; and
   (vi) assessing hypersensitivity and allergic reactions by graded histological changes in the 3-D skin equivalent model as compared to a control, wherein an increase of a graded histological reaction in the 3-D skin equivalent model identifies the test compound as a sensitizer, wherein the 3-D skin equivalent model comprises a scaffold, wherein the scaffold comprises a polystyrene support, and wherein the chemical compound is selected from a chemical, therapeutic, pharmaceutical, biologic, antibody or cosmetic agent, substance, preparation or composition.

2. The method of claim 1, wherein the T cells and monocyte-derived dendritic cells (DCs) are isolated from peripheral blood mononuclear cells (PBMC).

3. The method of claim 1, wherein the first incubating step of step (ii) is for between 2 to 24 hours.

4. The method of claim 1, wherein the second incubating of step (iii), comprising incubating DCs with a population of T cells isolated in step (i) is for between 3-7 days using the same culture conditions as for step (ii) except that 10% heat inactivated autologous serum, human AB serum, or an equivalent thereof is used in step (iii) and foetal calf serum is used in step ii).

5. The method of claim 1, wherein the step of assessing hypersensitivity and allergic reactions in the 3-D skin equivalent model by graded histological changes comprises assessment of vacuolisation of epidermal cells, damage to basal keratinocytes and connection between the epidermis and dermis.

6. The method of claim 1, wherein the control value may be derived from the group comprising:

(i) a further or second set of monocyte-derived dendritic cells that have been incubated in step (ii) with a compound that is a known non-sensitizer;
(ii) a further or second set of monocyte-derived dendritic cells that have been incubated in step (ii) with no additional chemical compounds;
(iii) a 3-D skin equivalent model that has been incubated with autologous lymphocytes; or
(iv) a skin 3-D skin equivalent model that has been incubated with compound alone at the same concentrations as that used in step (ii).

* * * * *